United States Patent [19]

Elliott

[11] 4,384,573

[45] May 24, 1983

[54] METHOD OF USING A SURGICAL DRAPE

[76] Inventor: Eugene D. Elliott, 159 Sherland Ave., Mountain View, Calif. 94043

[21] Appl. No.: 339,908

[22] Filed: Jan. 18, 1982

Related U.S. Application Data

[62] Division of Ser. No. 117,841, Feb. 1, 1980.

[51] Int. Cl.³ .............................................. A61B 19/08
[52] U.S. Cl. .................................................. 128/132 D
[58] Field of Search ............... 128/132 D, 132 R, 292, 128/303 R; 150/52 R

[56] References Cited

U.S. PATENT DOCUMENTS

| | | | |
|---|---|---|---|
| 1,257,332 | 2/1918 | Erlandson | 128/132 D X |
| 3,060,932 | 10/1962 | Pereny et al. | 128/132 D |
| 3,575,407 | 4/1971 | Carson | 128/132 D X |
| 3,799,161 | 3/1974 | Collins | 128/132 D |

*Primary Examiner*—Michael H. Thaler
*Attorney, Agent, or Firm*—Flehr, Hohbach, Test, Albritton & Herbert

[57] ABSTRACT

A method of covering a patient in preparation for surgery is disclosed herein along with a particular surgical drape utilized for this purpose. The surgical drape includes a flexible cover, preferably one which is light opaque and a closed light transparent window in the cover at a specific location. The cover is placed over the patient such that the window extends over the patient's face for observation by the surgical team.

4 Claims, 3 Drawing Figures

U.S. Patent  May 24, 1983  4,384,573
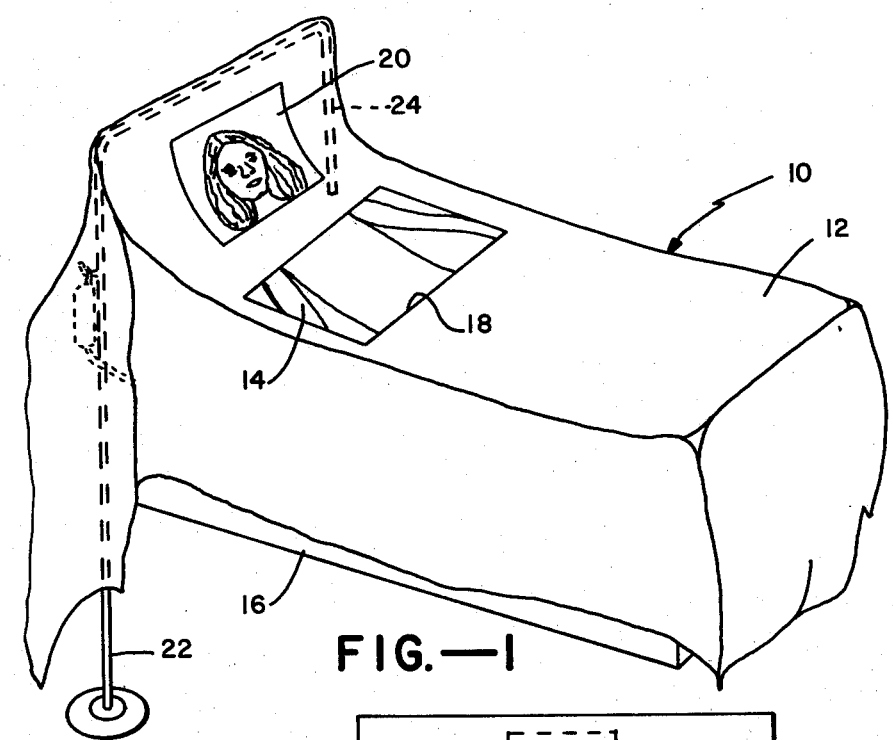
FIG.—1
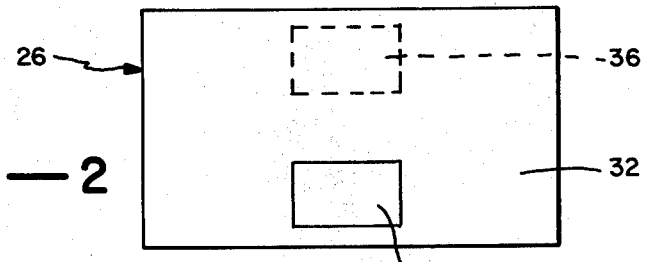
FIG.—2
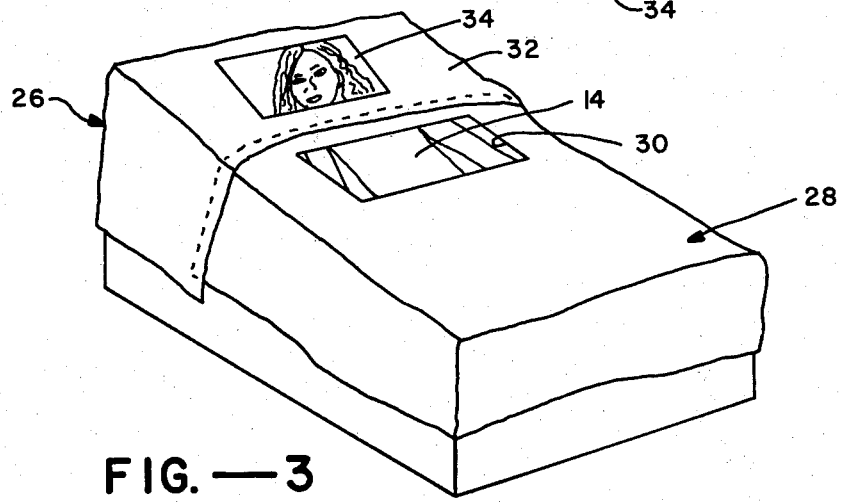
FIG.—3

METHOD OF USING A SURGICAL DRAPE

This is a division of application Ser. No. 117,841, filed Feb. 1, 1980.

The present invention relates generally to surgical drapes and more particularly to a specfic surgical drape and its method of use.

In performing surgery, other than head surgery, it is common to cover the patient entirely and provide an opening only at the location where surgery is to take place. An example of this may be seen in U.S. Pat. No. 3,799,161 which issued to Robert F. Collins, Mar. 26, 1974. There, a surgical drape is disclosed including a flexible main sheet having a plurality of openings (fenestrations) for performing a plurality of separate surgical procedures through the main sheet. The drape also includes a plurality of cover sheets which are removably secured to the upper surface of the main sheet over the openings, whereby all but a selected opening may be closed. One major problem with the surgical drape of the type described in the Collins patent is that during a surgical procedure (other than head surgery), the surgeon and his team can see and observe the patient's facial expressions or color or facial equipment associated with the anaesthetic without lifting up the drape. In the case of head surgery, the entire head is usually completely covered, with the exception of the specific localized area where surgery is to take place. Again, this procedure does not allow for continuous observation of the rest of the patient's head, including his face.

In some cases the head is not covered at all, as in U.S. Pat. No. 3,799,161. There, an anaesthesiology screen separates the head from the rest of the body including the area where surgery is to take place. While the head is not covered in this case, the surgeon cannot continuously view the patient's face or head equipment without purposely moving around the screen. This is an important drawback when an anesthesiologist is not present.

In view of the foregoing, it is the object of the present invention to eliminate the previously recited drawbacks by providing a surgical drape (and its method of use) which allows the surgeon to observe the patient's face and head while performing surgery even though the patient's head lies entirely under the drape or is obscured by part of the drape from the surgeon.

As will be seen hereinafter, the surgical drape disclosed herein and designed in accordance with a preferred embodiment includes a flexible, light opaque cover and a closed light transparent window in the cover at a first location, specifically over the face of the patient. In a second embodiment the cover also includes an opening at a second location, specifically at a location where surgery is to take place. In either case, the surgical drape can also be used in surgical procedures which require only a local anaesthetic. In these cases, the drape can be used to cover the patient's head in order to prevent him from viewing the surgery. At the same time, the surgical team can view the patient's facial expression and color through the window while the latter also serves to reduce claustrophobia to the patient.

The surgical drape and its method of use will be described in more detail with respect to the drawings comprising part of the specification wherein:

FIG. 1 is a perspective view of a surgical drape designed in accordance with one embodiment of the present invention and illustrated over a patient;

FIG. 2 is a top plan view of a surgical drape designed in accordance with a second, preferred embodiment; and FIG. 3 is a perspective view of the drape of FIG. 2 shown over a patient.

Turning to FIG. 1, the surgical drape illustrated there is generally designated by the reference numeral 10. The drape is comprised of a flexible, light opaque cover 12 having a topside and a bottomside and adapted for positioning in a predetermined way over a patient generally indicated at 14. The patient is shown in FIG. 1 on a surgical table 16.

In accordance with the present invention, surgical drape 10 also includes an opening 18 through cover 12 at a location where surgery is to take place, for example in the vicinity of the chest. The drape also includes a closed transparent window 20 in the cover at a location directly above the patient's head when the cover is oriented properly with respect to the patient. In this manner, the patient can be entirely covered in preparation for surgery by placing cover 12 entirely over the patient when the latter is lying on the surgical table such that the opening 18 extends over the appropriate area of surgery for access by the surgeon and such that window 20 extends over the patient's head and face for observation during surgery. In the embodiment shown, the top (head) end of the drape is positioned over and supported by two IV support stands generally indicated at 22 and 24. The top of these stands extend sufficiently above the patient so that window 12 extends up above the patient's head at an incline with the horizontal.

In a preferred embodiment of the present invention, flexible cover 12 is constructed of conventionally provided material, e.g. paper or cloth, or a combination of both and window 20 is preferably a clear, sterilizable vinyl plastic or the like. The surgical drape illustrated in FIG. 1 is approximately 8 feet long and 5 feet wide. Window 20 is preferably about 18 inches long and about 12 inches wide. The window material may be fixedly attached to cover 12 around the cooperating opening by means of adhesive.

While it is possible to initially provide surgical drape 10 as shown in the drawing, that is, with a prelocated opening 18 along with observation window 20, this requires the necessity to stock different surgical drapes for different surgical procedures. The surgical drape 10 designed in accordance with the present invention could be initially made with only observation window 20 and no opening 18. The opening could be provided later at the appropriate location in cover 12 depending upon its intended use. In this regard, cover 12 is preferably formed from a material which is readily cutable by means of a scissors or the like so that such an opening can be easily provided manually. The particular material recited in the preferred embodiment above is such a material.

Having described surgical drape 10 and its method of use, attention is now directed to another surgical drape illustrated in FIGS. 2 and 3 and generally designated by the reference numeral 26. This latter drape is primarily provided for covering only the patient's head as illustrated in FIG. 3. As shown there, the patient is covered by a conventional surgical drape 28 which extends approximately to the neck of the patient and which includes an appropriately located opening 30 corresponding to previously described opening 18. The surgical drape 26 which is entirely separate from drape 28 consists of a light opaque cover 32 and a window 34 appropriately incorporated into the cover (in the same manner as window 20) so as to be located over the head of the patient when the drape is provided over the patient in the manner shown. Both the cover 32 and the window 34 may be identical to previously described cover 12 and window 20 in drape 10 in all respects, except possibly for size. In a preferred embodiment, cover 32 is about 6 feet wide (across the patient) and 4 feet long (lengthwise of the patient). Window 34 is 10 inches wide and 12 inches long. Also, in this preferred embodiment, the window is centrally located with respect to the lengthwise edges of the cover but closer to one lateral edge than the other, for example as close as 10 inches (or less) from its closer edge. In this way, the drape can be positioned over the patient as shown in FIG. 3 in that the closer lateral edge is just under the patient's head or so that the closer lateral edge is behind the patient'head. In this latter case, cover 32 could be provided with an opening 36 indicated by dotted lines in FIG. 2 for providing access to the chest area for providing surgery thereat. In this way drape 26 functions in the same way as drape 10.

The design of each of the surgical drapes 10 and 26 as described above presupposes that cover 12 (in the case of drape 10) and cover 32 (in the case of drape 26) are constructed of light opaque material. If the cover itself is transparent it would serve as the transparent window as well as a cover. In this way, a separate window would not be necessary.

I claim:

1. In a method of performing surgery on a patient below the patient's head while he is lying on his back on a surgical table, the improvement comprising: providing a surgical drape including a flexible cover having one portion including at least a section which is light transparent and which serves as a closed, light transparent observation window; positioning said flexible cover over at least a part of the patient in a predetermined way such that said observation window is placed over and above the face of said patient; providing an opening in a second portion of said cover in the location on the patient where surgery is to take place; and performing surgery through said opening while observing the face of said patient through said window.

2. A method according to claim 1 wherein said one portion includes a light opaque section surrounding said window.

3. A method according to claim 1 wherein said flexible cover is entirely light opaque with the exception of said window and said opening.

4. A method according to claim 3 wherein said opening is provided before said cover is placed on said patient.

* * * * *